US010053719B2

(12) United States Patent
Saaem et al.

(10) Patent No.: US 10,053,719 B2
(45) Date of Patent: Aug. 21, 2018

(54) COMPOSITIONS AND METHODS FOR SYNTHESIS OF HIGH FIDELITY OLIGONUCLEOTIDES (71) Applicant: Gen9, Inc., Cambridge, MA (US)

(72) Inventors: Ishtiaq E. Saaem, Dhaka (BD); Michael E. Hudson, Framingham, MA (US); Stephen F. Archer, Cambridge, MA (US); Sophea Sann-Rorth, Revere, MA (US); Ellen J. Sanchez, North Andover, MA (US); Joseph Jacobson, Newton, MA (US)

(73) Assignee: Gen9, Inc., Cambridge, MA (US)

( * ) Notice: Subject to any disclaimer, the term of this patent is extended or adjusted under 35 U.S.C. 154(b) by 117 days.

(21) Appl. No.: 14/765,978

(22) PCT Filed: Mar. 13, 2014

(86) PCT No.: PCT/US2014/025737
§ 371 (c)(1),
(2) Date: Aug. 5, 2015

(87) PCT Pub. No.: WO2014/160059
PCT Pub. Date: Oct. 2, 2014

(65) Prior Publication Data
US 2015/0368687 A1    Dec. 24, 2015

Related U.S. Application Data (60) Provisional application No. 61/851,759, filed on Mar. 13, 2013.

(51) Int. Cl.
*C12P 19/34* (2006.01)
*C12N 15/10* (2006.01)
*C12N 15/66* (2006.01)

(52) U.S. Cl.
CPC .............. *C12P 19/34* (2013.01); *C12N 15/10* (2013.01); *C12N 15/1031* (2013.01); *C12N 15/66* (2013.01)

(58) Field of Classification Search
None
See application file for complete search history.

(56) References Cited

U.S. PATENT DOCUMENTS

| 7,323,320 | B2 | 1/2008 | Oleinikov |
| 7,563,600 | B2 | 7/2009 | Oleinikov |
| 8,058,004 | B2 | 11/2011 | Oleinikov |
| 8,349,587 | B2 | 1/2013 | Fischer et al. |
| 8,716,467 | B2 | 5/2014 | Jacobson |
| 8,808,986 | B2 | 8/2014 | Jacobson et al. |
| 9,023,601 | B2 | 5/2015 | Oleinikov |
| 9,051,666 | B2 | 6/2015 | Oleinikov |
| 9,187,777 | B2 | 11/2015 | Jacobson et al. |
| 9,216,414 | B2 | 12/2015 | Chu |
| 9,217,144 | B2 | 12/2015 | Jacobson et al. |
| 9,388,407 | B2 | 7/2016 | Jacobson |
| 9,422,600 | B2 | 8/2016 | Ramu et al. |
| 9,506,167 | B2 | 11/2016 | Shetty et al. |
| 2004/0161742 | A1 | 8/2004 | Dean et al. |
| 2005/0176023 | A1 | 8/2005 | Ramon et al. |
| 2007/0031857 | A1 | 2/2007 | Makarov et al. |
| 2011/0217738 | A1 | 9/2011 | Jacobson |
| 2012/0070870 | A1 | 3/2012 | Way et al. |
| 2012/0220497 | A1 | 8/2012 | Jacobson et al. |
| 2013/0244884 | A1 | 9/2013 | Jacobson et al. |
| 2014/0309119 | A1 | 10/2014 | Jacobson et al. |
| 2015/0037853 | A1 | 2/2015 | Fischer et al. |
| 2015/0315599 | A1 | 11/2015 | Shetty et al. |
| 2015/0376602 | A1 | 12/2015 | Jacobson et al. |
| 2016/0001247 | A1 | 1/2016 | Oleinikov |
| 2016/0097051 | A1 | 4/2016 | Jacobson et al. |
| 2016/0122755 | A1 | 5/2016 | Hall et al. |
| 2016/0144332 | A1 | 5/2016 | Chu |
| 2016/0144333 | A1 | 5/2016 | Jacobson et al. |
| 2016/0168564 | A1 | 6/2016 | Jacobson et al. |
| 2016/0215318 | A1 | 7/2016 | Jacobson |
| 2016/0326520 | A1 | 11/2016 | Ramu et al. |
| 2017/0074889 | A1 | 3/2017 | Shetty et al. |
| 2017/0173086 | A1 | 6/2017 | Boyle et al. |
| 2017/0240886 | A1 | 8/2017 | Oleinikov |

FOREIGN PATENT DOCUMENTS

| WO | WO-2004/024886 A2 | 3/2004 |
| WO | 2005030983 | 4/2005 |
| WO | WO-2010/025310 A2 | 3/2010 |
| WO | WO-2010/141468 A1 | 12/2010 |
| WO | WO-2011/056872 A2 | 5/2011 |
| WO | WO-2011/066185 A1 | 6/2011 |
| WO | WO-2011/066186 A1 | 6/2011 |
| WO | WO-2011/085075 A2 | 7/2011 |
| WO | WO-2011/143556 A1 | 11/2011 |
| WO | WO-2011/150168 A1 | 12/2011 |
| WO | 2013032850 | 3/2013 |
| WO | WO-2013/066848 A1 | 5/2013 |
| WO | WO-2014/089436 A1 | 6/2014 |
| WO | WO-2014/151696 A1 | 9/2014 |
| WO | WO-2014/160004 A1 | 10/2014 |
| WO | WO-2014/160059 A1 | 10/2014 |
| WO | WO-2015/017527 A2 | 2/2015 |
| WO | WO-2015/148680 A1 | 10/2015 |

OTHER PUBLICATIONS

International Preliminary Report of Patentability issued in International Patent Application PCT/US2014/025737 dated Sep. 24, 2015.
International Search Report for International Application No. PCT/2014/025737 dated Aug. 20, 2014.
Written Opinion for PCT/2014/025737, 8 pages (dated Aug. 20, 2014).

*Primary Examiner* — David C Thomas (74) *Attorney, Agent, or Firm* — Choate, Hall & Stewart LLP; Brenda Herschbach Jarrell; Robert N. Sahr (57) ABSTRACT

Aspects of the invention relate to methods, compositions for synthesizing high fidelity oligonucleotides.

14 Claims, 7 Drawing Sheets

COMPOSITIONS AND METHODS FOR SYNTHESIS OF HIGH FIDELITY OLIGONUCLEOTIDES

RELATED APPLICATIONS

This application is a National Phase application of International Application No. PCT/US2014/025737, filed Mar. 13, 2014 which claims the benefit of and priority to U.S. Provisional Application No. 61/851,759, filed Mar. 13, 2013, the contents of each foregoing applications are incorporated herein by reference in their entirety.

FIELD OF THE INVENTION

Methods and compositions of the invention relate to the synthesis of high fidelity oligonucleotides and particularly to high fidelity primers.

BACKGROUND

Recombinant and synthetic nucleic acids have many applications in research, industry, agriculture, and medicine. Recombinant and synthetic nucleic acids can be used to express and obtain large amounts of polypeptides, including enzymes, antibodies, growth factors, receptors, and other polypeptides that may be used for a variety of medical, industrial, or agricultural purposes. Recombinant and synthetic nucleic acids also can be used to produce genetically modified organisms including modified bacteria, yeast, mammals, plants, and other organisms. Genetically modified organisms may be used in research (e.g., as animal models of disease, as tools for understanding biological processes, etc.), in industry (e.g., as host organisms for protein expression, as bioreactors for generating industrial products, as tools for environmental remediation, for isolating or modifying natural compounds with industrial applications, etc.), in agriculture (e.g., modified crops with increased yield or increased resistance to disease or environmental stress, etc.), and for other applications. Recombinant and synthetic nucleic acids also may be used as therapeutic compositions (e.g., for modifying gene expression, for gene therapy, etc.) or as diagnostic tools (e.g., as probes for disease conditions, etc.).

Numerous techniques have been developed for modifying existing nucleic acids (e.g., naturally occurring nucleic acids) to generate recombinant nucleic acids. For example, combinations of nucleic acid amplification, mutagenesis, nuclease digestion, ligation, cloning and other techniques may be used to produce many different recombinant nucleic acids. Chemically synthesized polynucleotides are often used as primers or adaptors for nucleic acid amplification, mutagenesis, and cloning.

Techniques also are being developed for de novo nucleic acid assembly whereby nucleic acids are made (e.g., chemically synthesized) and assembled to produce longer target nucleic acids of interest. For example, different multiplex assembly techniques are being developed for assembling oligonucleotides into larger synthetic nucleic acids that can be used in research, industry, agriculture, and/or medicine. However, one limitation of currently available assembly techniques is the relatively high error rate in synthetic oligonucleotides.

SUMMARY OF THE INVENTION

Some aspects of the invention relate to methods for synthesizing high fidelity target oligonucleotides. According to various embodiments, an array is provided, the array comprising a plurality of nucleic acids, each nucleic acid having a sequence comprising a template oligonucleotide sequence and a primer binding sequence, wherein the template oligonucleotide sequence is a reverse complement of the target oligonucleotide. In some embodiments, the primer binding site is 3' or 5' of the template sequence. In some embodiments, the primer binding region is at least 100 bps long. In some embodiments, the primer binding region is about 200 bps long. In some embodiments, the primer binding region is ligated to the template oligonucleotide.

In some embodiments, the plurality of nucleic acids is synthesized on the array. The plurality of nucleic acids can be synthesized in a 3'→5' or in a 5'→3' direction. For example, the plurality of nucleic acids is synthesized in a 3'→5' direction onto the array, thereby immobilizing the nucleic acids by their 3' terminus. In some embodiments, each nucleic acid of the plurality of nucleic acids is phosphorylated at the 3' end. In some embodiments, the array comprises a porous reaction layer coupled to a phosphorylation reagent.

The plurality of nucleic acids can be released from the array. In some embodiments, the method comprises dephosphorylating the 3' end of the nucleic acids and phosphorylating the 5' end of the nucleic acids. The nucleic acids can then be circularized, for example in the presence of a ligase. In some embodiments, a primer is provided. The primer, in various embodiments, can comprise a sequence complementary to the primer binding sequence, a restriction enzyme recognition site and self-complementary termini. In some embodiments, the primer is provided under conditions promoting annealing of the primer to the primer binding sites. In some embodiments, the primer is a universal primer. In some embodiments, the primer binding sequence or region is at least 100 bps long. In some embodiments, the primer binding sequence is about 200 bps long. In some embodiments, the primer binding region is ligated to the template oligonucleotide. In some embodiments, the primers contain dT-biotin.

After amplification of the circularized oligonucleotide in rolling-circle amplification reaction using the primer, the primer sequences of the amplified nucleic acids can be removed under conditions promoting hairpin formation of the primer. The target oligonucleotide can be isolated.

In some embodiments, the plurality of nucleic acids is released in a pool. In some embodiments, the nucleic acids are purified. In some embodiments, the nucleic acids are isolated using streptavidin beads binding the biotin moieties. In some embodiments, the streptavidin beads can bind the biotinylated primers.

According to some aspects of the invention, the method comprises providing a plurality of nucleic acids, each nucleic acid comprising a template sequence, a 5' end flanking regions and a 3' end flanking region, wherein the 5' end flanking region comprises a first primer binding sequence and the 3' end flanking region comprises a second primer binding sequence and a restriction enzyme recognition site. The method can further comprise providing a first primer capable of annealing the first binding sequence and a second primer capable of annealing to the second primer binding sequence, the first primer comprising biotin at the 5' end and Uracil at the 3' end. The nucleic acids can then be amplified to form a plurality of double-stranded nucleic acids and the second primer binding sequence can be removed by enzymatic cleavage using a suitable restriction enzyme. The plurality of digested nucleic acids can be isolated using a solid support comprising streptavidin. The resulting product can then be denatured to form a plurality of single-stranded nucleic acids. The uracil can be removed at the 5' end of the plurality of single-stranded nucleic acids using a DNA-glycosylase and endonuclease. The single-stranded nucleic acids can then be released from the solid support. For example, the single-stranded nucleic acids can then be released from the solid support by heating to break abasic bonds. Release from the solid support can also be effected chemically or photochemically given the appropriate choice of attachment linkers.

In some embodiments, the plurality of nucleic acids can be provided on an array. In some embodiments, the primers can be universal or semi-universal primers.

According to some aspects of the invention, the methods can further comprise subjecting the double-stranded nucleic acids to error removal. In some embodiments, the double-stranded nucleic acids can be subjected to error removal by using a MutS or MutS homologs.

BRIEF DESCRIPTION OF THE FIGURES

FIGS. 1A-1B illustrate an exemplary method for the synthesis of high fidelity oligonucleotides according to a non-limiting embodiment.

DETAILED DESCRIPTION OF THE INVENTION

Aspects of the invention relate to methods and compositions for the synthesis of high fidelity, high quality oligonucleotides. Certain aspects of the invention relate to methods and compositions for the synthesis of high fidelity oligonucleotide primers. In some aspects of the invention, the methods and compositions can be used to assemble large numbers of nucleic acid fragments efficiently, and/or to reduce assembly error rate. Methods of the invention can be incorporated into nucleic assembly procedures to increase assembly fidelity, throughput and/or efficiency, decrease cost, and/or reduce assembly time. In some embodiments, the methods of the invention may be automated and/or implemented in a high throughput assembly context to facilitate parallel production of many different target nucleic acid products.

As used herein, an oligonucleotide may be a nucleic acid molecule comprising at least two covalently bonded nucleotide residues. The terms "oligonucleotide', "polynucleotide" and "nucleic acid" are used interchangeably. In some embodiments, an oligonucleotide may be between 10 and 1,000 nucleotides long. For example, an oligonucleotide may be between 10 and 500 nucleotides long, or between 500 and 1,000 nucleotides long. In some embodiments, an oligonucleotide may be between about 20 and about 300 nucleotides long (e.g., from about 30 to 250, 40 to 220, 50 to 200, 60 to 180, or about 65 or about 150 nucleotides long), between about 100 and about 200, between about 200 and about 300 nucleotides, between about 300 and about 400, or between about 400 and about 500 nucleotides long. However, shorter or longer oligonucleotides may be used. An oligonucleotide may be a single-stranded nucleic acid. However, in some embodiments, a double-stranded oligonucleotide may be used as described herein. In certain embodiments, an oligonucleotide may be chemically synthesized as described in more detail below. In some embodiments, nucleic acids (e.g., synthetic oligonucleotide) may be amplified before use. The resulting product may be double-stranded.

Typically, oligonucleotide synthesis involves a number of chemical steps that are performed in a cycle repetitive manner throughout the synthesis, with each cycle adding one nucleotide to the growing oligonucleotide chain. The chemical steps involved in a cycle are a deprotection step that liberates a functional group for further chain elongation, a coupling step that incorporates a nucleotide into the oligonucleotide to be synthesized, and other steps as required by the particular chemistry used in the oligonucleotide synthesis, such as, for example, an oxidation step required with the phosphoramidite chemistry. Optionally, a capping step that blocks those functional groups which were not elongated in the coupling step can be inserted in the cycle. The nucleotide can be added to the 5'-hydroxyl group of the terminal nucleotide, in the case in which the oligonucleotide synthesis is conducted in a 3'→5' direction or at the 3'-hydroxyl group of the terminal nucleotide in the case in which the oligonucleotide synthesis is conducted in a 5'→3' direction.

For clarity, the two complementary strands of a double stranded nucleic acid are referred to herein as the positive (P) and negative (N) strands. This designation is not intended to imply that the strands are sense and anti-sense strands of a coding sequence. They refer only to the two complementary strands of a nucleic acid (e.g., a target nucleic acid, an intermediate nucleic acid fragment, etc.) regardless of the sequence or function of the nucleic acid. Accordingly, in some embodiments a P strand may be a sense strand of a coding sequence, whereas in other embodiments a P strand may be an anti-sense strand of a coding sequence. It should be appreciated that the reference to complementary nucleic acids or complementary nucleic acid regions herein refers to nucleic acids or regions thereof that have sequences which are reverse complements of each other so that they can hybridize in an antiparallel fashion typical of natural DNA.

In some aspects of the invention, the synthetic oligonucleotides synthesized according to the methods described herein can be used as primers for sequencing reactions (for example, next generation sequencing reactions), or as building blocks for the assembly of a target nucleic acid of interest.

Synthesis of Oligonucleotides on Solid Support

Oligonucleotides may be synthesized on solid support. As used herein, the term "support" and "substrate" are used interchangeably and refers to a porous or non-porous solvent insoluble material on which polymers such as nucleic acids are synthesized or immobilized. As used herein "porous" means that the material contains pores having substantially uniform diameters (for example in the nm range). Porous materials can include but are not limited to, paper, synthetic filters and the like. In such porous materials, the reaction may take place within the pores. The support can have any one of a number of shapes, such as pin, strip, plate, disk, rod, bends, cylindrical structure, particle, including bead, nanoparticle and the like. The support can have variable widths.

The support can be hydrophilic or capable of being rendered hydrophilic. The support can include inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly (4-methylbutene), polystyrene, polymethacrylate, poly(ethylene terephthalate), nylon, poly(vinyl butyrate), polyvinylidene difluoride (PVDF) membrane, glass, controlled pore glass, magnetic controlled pore glass, ceramics, metals, and the like; either used by themselves or in conjunction with other materials.

In some embodiments, pluralities of different single-stranded oligonucleotides are immobilized at different features of a solid support. In some embodiments, the support-bound oligonucleotides may be attached through their 5' end or their 3' end. In some embodiments, the support-bound oligonucleotides may be immobilized on the support via a nucleotide sequence (e.g. degenerate binding sequence), linker (e.g. photocleavable linker or chemical linker). It should be appreciated that by 3' end, it is meant the sequence downstream to the 5' end and by 5' end it is meant the sequence upstream to the 3' end. For example, an oligonucleotide may be immobilized on the support via a nucleotide sequence or linker that is not involved in subsequent reactions.

Certain embodiments of the invention may make use of a solid support comprised of an inert substrate and a porous reaction layer. The porous reaction layer can provide a chemical functionality for the immobilization of presynthesized oligonucleotides or for the synthesis of oligonucleotides. In some embodiments, the surface of the array can be treated or coated with a material comprising suitable reactive group for the immobilization or covalent attachment of nucleic acids. Any material, known in the art, having suitable reactive groups for the immobilization or in situ synthesis of oligonucleotides can be used.

In some embodiments, the porous reaction layer can be treated so as to comprise hydroxyl reactive groups. For example, the porous reaction layer can comprise sucrose.

According to some aspects of the invention, oligonucleotides terminated with a 3' phosphoryl group oligonucleotides can be synthesized a 3'→5' direction on a solid support having a chemical phosphorylation reagent attached to the solid support. In some embodiments, the phosphorylation reagent can be coupled to the porous layer before synthesis of the oligonucleotides. In an exemplary embodiment, the phosphorylation reagent can be coupled to the sucrose. For example, the phosphorylation reagent can be 2-[2-(4,4'-Dimethoxytrityloxy)ethylsulfonyl]ethyl-(2-cyanoethyl)-(N,N-diisopropyl)-phosphoramidite. In some embodiments, the 3' phosphorylated oligonucleotide can be released from the solid support and may undergo subsequent modifications according to the methods described herein. In some embodiments, the 3' phosphorylated oligonucleotide can be released from the solid support using ammonium hydroxide.

In some embodiments, synthetic oligonucleotides for the assembly may be designed (e.g. sequence, size, and number). Synthetic oligonucleotides can be generated using standard DNA synthesis chemistry (e.g. phosphoramidite method). Synthetic oligonucleotides may be synthesized on a solid support, such as, for example, a microarray, using any appropriate technique as described in more detail herein. Oligonucleotides can be eluted from the microarray prior to be subjected to amplification or can be amplified on the microarray. It should be appreciated that different oligonucleotides may be designed to have different lengths.

In some embodiments, oligonucleotides are synthesized on an array format. For example, single-stranded oligonucleotides are synthesized in situ on a common support wherein each oligonucleotide is synthesized on a separate or discrete feature (or spot) on the substrate. In preferred embodiments, single-stranded oligonucleotides are bound to the surface of the support or feature. As used herein, the term "array" refers to an arrangement of discrete features for storing, routing, amplifying and releasing oligonucleotides or complementary oligonucleotides for further reactions. In a preferred embodiment, the support or array is addressable: the support includes two or more discrete addressable features at a particular predetermined location (i.e., an "address") on the support. Therefore, each oligonucleotide molecule of the array is localized to a known and defined location on the support. The sequence of each oligonucleotide can be determined from its position on the support. Moreover, addressable supports or arrays enable the direct control of individual isolated volumes such as droplets. The size of the defined feature can be chosen to allow formation of a microvolume droplet on the feature, each droplet being kept separate from each other. As described herein, features are typically, but need not be, separated by interfeature spaces to ensure that droplets between two adjacent features do not merge. Interfeatures will typically not carry any oligonucleotide on their surface and will correspond to inert space. In some embodiments, features and interfeatures may differ in their hydrophilicity or hydrophobicity properties.

Synthetic Oligonucleotides

In some embodiments, 3' phosphorylated oligonucleotides may be synthesized in situ. In other embodiments, the oligonucleotides can be chemically phosphorylated post-synthesis. In some embodiments, 5' phosphorylated oligonucleotides can be synthesized in situ. For example, the 5' phosphate group can be attached to the oligonucleotide in the last coupling cycle with a phosphorylation reagent. In other embodiments, oligonucleotides may be phosphorylated (e.g., with a 5' phosphate) post-synthesis. The oligonucleotides can be chemically phosphorylated or enzymatically phosphorylated. In some embodiments, an oligonucleotide may be non-phosphorylated.

Oligonucleotides may be provided or synthesized as single-stranded synthetic products. In some embodiments, oligonucleotides may also be provided or synthesized as double-stranded preparations including an annealed complementary strand. Oligonucleotides may be molecules of DNA, RNA, PNA, or any combination thereof. A double-stranded oligonucleotide may be produced by amplifying a single-stranded synthetic oligonucleotide or other suitable template (e.g., a sequence in a nucleic acid preparation such as a nucleic acid vector or genomic nucleic acid). Accordingly, a plurality of oligonucleotides designed to have the sequence characteristics described herein may be provided as a plurality of single-stranded oligonucleotides having those characteristics, or also may be provided along with complementary oligonucleotides.

In some embodiments, the single-stranded oligonucleotides can be amplified to form double-stranded oligonucleotides. In some embodiments, nucleic acid sequences comprising the positive and negative strands can be synthesized on a solid support.

In some embodiments, a synthetic nucleic acid may include an internal sequence of interest (or payload) flanked by 5' end and/or 3' end amplification sequences. The flanking sequences are designed for amplification purposes. The flanking amplification sequences may be used as universal primer sequences to amplify a plurality of different oligonucleotides that share the same amplification sequences but have different internal sequences. In some embodiments, the flanking sequences are removed after amplification to produce an oligonucleotide(s) having the desired sequence. In certain embodiments, the nucleic acid sequence may comprise the reverse complement sequence and a primer binding sequence at the 5' end or the 3' end of the reverse complement oligonucleotide sequence (also referred herein as template oligonucleotide). As used herein, the terms "primer binding sequence", "primer binding region" and "primer binding site" can be used interchangeably. Alternatively, the nucleic acid may comprise the reverse complement oligonucleotide sequence and a primer binding sequence at the 5' end and at the 3' end of the template oligonucleotide.

In some embodiments, the nucleic acids may be designed to contain a central sequence flanked by a 5' amplification sequence (e.g., a 5' universal sequence) and/or a 3' amplification sequence (e.g., a 3' universal sequence). Amplification primers (e.g., between 10 and 50 nucleotides long, between 15 and 45 nucleotides long, about 25 nucleotides long, etc.) corresponding to the flanking amplification sequences may be used to amplify the nucleic acids. For example, one primer may be complementary to the 3' amplification sequence and one primer may have the same sequence as the 5' amplification sequence. In some embodiments, the nucleic acids may be amplified using an appropriate primer pair with one primer corresponding to each end of the oligonucleotide. For example, one primer can be complementary to the 3' end of the oligonucleotide and one primer can be identical to the 5' end of the oligonucleotide).

The amplification sequences may then be removed from the amplified oligonucleotide(s) using any suitable technique to produce an oligonucleotide(s) that contains only the central sequence.

The central sequence can be, according to some embodiments, designed to be incorporated into a longer target nucleic acid of interest. In some embodiments, a plurality of different oligonucleotides (e.g., about 5, 10, 50, 100, or more) with different central assembly sequences may have identical 5' amplification sequences and/or identical 3' amplification sequences. These oligonucleotides can all be amplified in the same reaction using the same amplification primers.

In certain embodiments, it may be helpful to include one or more modified primers. An oligonucleotide or primer may be modified by incorporating a modified-base (e.g., a nucleotide analog) during synthesis, by modifying the oligonucleotide after synthesis, or any combination thereof. Examples of modifications include, but are not limited to, one or more of the following: universal bases such as nitro indoles, dP and dK, inosine, uracil, halogenated bases such as BrdU, fluorescent labeled bases, non-radioactive labels such as biotin (as a derivative of dT or other nucleotides) and digoxigenin (DIG), 2,4-dinitrophenyl (DNP), radioactive nucleotides, post-coupling modification such as dR-NH2 (deoxyribose-NEb), Acridine (6-chloro-2-methoxiacridine), and spacer phosphoramides which are used during synthesis to add a spacer "arm" into the sequence, such as C3, C8 (octanediol), C9, C12, HEG (hexaethlene glycol) and C18.

In some embodiments, an abasic site can be created at a predetermined position on the primer region. This can be done by, for example, incorporating uracil (U) in one of the primer used for amplification. In some embodiments, one or two of the primers can comprise one or more uracil (U). The primer can be first annealed to a support-bound single-stranded oligonucleotide and extended with the addition of dNTPs and an appropriate polymerase under appropriate conditions and temperature. In a subsequent step, the primer can be removed. The nucleic acid to be cleaved can be exposed to a mixture of appropriate glycosylase and endonuclease. In some embodiments, uracil DNA glycosylase (UDG) may be used to hydrolyze a uracil-glycosidic bond in a nucleic acid thereby removing uracil and creating an alkali-sensitive abasic site in the DNA which can be subsequently hydrolyzed by endonuclease, heat or alkali treatment.

In some embodiments, the abasic sites can be introduced at the 3' end of the synthetic nucleic acid if the oligonucleotide synthesis is conducted in a 3'→5' direction. Cleavage of the abasic sites results in the release of the single stranded nucleic acids from the support. This method of cleavage has the advantage not to have to engineer the primer to include a restriction enzyme site that can be several nucleotides long.

In some embodiments, a portion of one strand of a double-stranded nucleic acid may be removed thereby exposing the complementary sequence in the form of a single-stranded overhang. This approach requires the deliberate incorporation of one or more uracil bases on one strand of a double-stranded nucleic acid fragment. This may be accomplished, for example, by amplifying a nucleic acid fragment using an amplification primer that contains a 3' terminal uracil. After treatment with UDG, the region of the primer 5' to the uracil may be released (e.g., upon dilution, incubation, exposure to mild denaturing conditions, etc.) thereby exposing the complementary sequence as a single-stranded overhang. It should be appreciated that the length of the overhang may be determined by the position of the uracil on the amplifying primer and by the length of the amplifying primer. In some embodiments, mixture of Uracil DNA glycosylase (UDG) and the DNA glycosylase-lyase Endonuclease VIII, such as USER™ (Uracil-Specific Excision Reagent) is used. UDG catalyses the excision of a uracil base, forming an abasic site while leaving the phosphodiester backbone intact. The lyase activity of Endonuclease VIII breaks the phosphodiester backbone at the 3' and 5' sides of the abasic site so that base-free deoxyribose is released.

Yet in some embodiments, the primer may be designed to include a restriction recognition sequence for a restriction enzyme. Essentially any restriction enzyme may be used.

After amplification, the polymerase may be deactivated to prevent interference with the subsequent steps. A heating step (e.g. high temperature) can denature and deactivate most enzymes which are not thermally stable. In some embodiments, a non-thermal stable version of the thermally stable PCR DNA Polymerase may be used, although the enzyme is less optimized for error rate and speed. Alternatively, Epoxy dATP can be used to inactivate the enzyme.

In the synthesis, defective nucleic acids can be produced as a consequence of, for example, premature termination of synthesis, which results in truncated molecules. In some embodiments, the nucleic acids can be modified such as only full length can circularize. In various embodiments, the method comprises enriching for full length nucleic acids. In some embodiments, 5' aldehyde-modified nucleic acids can be synthesized and His-tag can be attached to the aldehyde group. The reaction can be followed a 5'-biotin derivatization. For example, oligonucleotides can be biotinylated according to the methods described in York et al. (Nucleic Acids Research, 2012, Vol. 40, No. 1 e4), which is incorporated herein by reference in its entirety. Oligonucleotides lacking the His-tag or truncated nucleic acids can be removed by high pH wash.

Amplification and Removal of Primer Sequences

In some embodiments, the oligonucleotides may be amplified on the solid support or in solution. Oligonucleotides may be released or cleaved from the support prior to amplification or after amplification.

In certain embodiments, the double-stranded amplification products may be subject to restriction enzyme digestion to remove the flanking sequences. To that end, the flanking sequences can be designed to include one or more restriction sites or restriction enzyme recognition sites. The restriction site may be present at the 5' or 3' end of the amplification sequence as long as the cleavage site is between the flanking sequence to be removed and the internal sequence. The restriction site may be included in the amplification sequence (i.e., primer binding site). The restriction site may also be outside the amplification sequence.

After restriction enzyme digestion, the cleaved flanking sequences may be separated and removed using any suitable technique. In some embodiments, the cleaved flanking sequences may be fragments less than about 40, about 35, about 30, about 25, about 20, or about 15 bases long. As such, size dependent separation techniques known in the art may be used, such as differential affinity to silica, size filtration, differential precipitation with PEG (polyethylene glycol) or CTAB (cetyltrimethlyammonium bromide), or any combination thereof, so as to separate the cleaved flanking sequences from the central assembly sequences that can be designed to be longer in size than the flanking sequences.

In some embodiments, the amplification primers may be biotinylated. In some embodiments, one amplification primer is biotinylated. Oligonucleotides can be biotinylated according to methods known in the art. For example, oligonucleotides can be biotinylated according to the methods described in York et al. (Nucleic Acids Research, 2012, Vol. 40, No. 1 e4), which is incorporated herein by reference in its entirety.

In some embodiments, the upstream or forward primer can be biotinylated thereby generating double-stranded nucleic acids which are biotinylated at their 5' end. In some embodiments, upon amplification, the biotinylated amplification products are released in solution. Thus, the amplification products can be affinity purified using streptavidin (e.g., bound to a bead, column, or other surface).

In certain embodiments, the amplification primers also may be designed to include certain sequence features (e.g., restriction sites) that can be used to remove the primer binding regions after amplification in order to produce a double-stranded assembly fragment that includes the sequence of interest without the flanking amplification sequence(s).

In some embodiments, the sequence of interest can be flanked with a single flanking region at the 5' or at the 3' end containing the primer binding regions. In some embodiments, the sequence of interest can be flanked with two flanking regions containing the primer binding regions at the 3' end (capable of binding an upstream or forward primer) and at the 5' end (capable of binding a downstream or reverse primer). In some embodiments, the upstream primer may be designed to be biotinylated at its 5' end and to comprise Uracil at its 3' end.

Error Reduction

A preparation of an oligonucleotide designed to have a certain sequence may include oligonucleotide molecules having the designed sequence in addition to oligonucleotide molecules that contain errors (e.g., that differ from the designed sequence at least at one position). A sequence error may include one or more nucleotide deletions, additions, substitutions (e.g., transversion or transition), inversions, duplications, or any combination of two or more thereof. Errors may be generated during oligonucleotide synthesis. Template oligonucleotides can have inherent errors as they are generally chemically synthesized (e.g., deletions at a rate of 1 in 100 bases and mismatches and insertions at about 1 in 400 bases). Assuming an average error rate of 1 in 300 bases and an average template oligonucleotide size of 70 bases, every 1 in 4 template oligonucleotides will contain an error compared to a reference sequence (e.g., the wild-type sequence of a gene of interest). For example, a template oligonucleotide can contain an error which can be a mismatch, deletion, or insertion. In PCR synthesis, the error is retained in the synthesized oligonucleotide. Additional errors can be introduced during PCR reactions.

It should be appreciated that different synthetic techniques may be prone to different error profiles and frequencies. In some embodiments, error rates may vary from 1/10 to 1/200 errors per base depending on the synthesis protocol that is used. However, in some embodiments, lower error rates may be achieved. Also, the types of errors may depend on the synthetic techniques that are used. For example, in some embodiments, chip-based oligonucleotide synthesis may result in relatively more deletions than column-based synthetic techniques.

Accordingly, methods for error correction are needed for high-fidelity oligonucleotide synthesis. In some embodiments, one or more oligonucleotide preparations may be subjected to an error reduction or error filtration process to remove (or reduce the number or the frequency of) error-containing oligonucleotides. Such process can be used to increase the number of error-free oligonucleotides in the oligonucleotide preparations. Methods for conducting error reduction or error filtration can include, for example, hybridization to a selection oligonucleotide, binding to a mismatch binding agent or to a mismatch binding protein or combinations thereof.

In some embodiments, error correction may be included at the end of the synthesis process to increase the relative population of synthesized oligonucleotides without deviation from the desired sequences. In some embodiments, error correction is included after amplification of the oligonucleotides. Yet in some embodiments, the positive and negative strands can be synthesized and error correction may be included after annealing of the positive and negative strands.

Such error correction may include direct sequencing and/or the application of error correction based on correcting enzymes, such as error correcting nucleases (e.g. CEL I and/or CEL II), error correction based on MutS or MutS homologs binding or other mismatch binding proteins (see, e.g., International Application No. PCT/US2010/057405), other means of error correction as known in the art or any combination thereof. In an exemplary embodiment, CEL I and/or CEL II may be added to the oligonucleotide duplexes in the fluid medium. CEL I and/or CEL II is a mismatch specific endonuclease that cleaves all types of mismatches such as single nucleotide polymorphisms, small insertions or deletions. Addition of the endonuclease results in the cleavage of the double-stranded oligonucleotides at the site or region of the mismatch.

It should be appreciated that synthetic oligonucleotides often have sequence errors. Accordingly, oligonucleotide preparations may be selected or screened to remove error-containing molecules as described in more detail herein. Error containing-oligonucleotides may be double-stranded homoduplexes having the error on both strands (i.e., incorrect complementary nucleotide(s), deletion(s), or addition(s) on both strands).

In some embodiments, mismatch recognition can be used to control the errors generated during oligonucleotide synthesis, gene assembly, and the construction of longer polynucleotides. After amplification of the support-bound nucleic acids, the nucleic acids duplexes can be first subjected to round(s) of melting and annealing (also referred herein as shuffling). In some embodiments, sequence errors may be removed using a technique that involves denaturing and reannealing the double-stranded nucleic acids. In some embodiments, single strands of nucleic acids that contain complementary errors may be unlikely to reanneal together if nucleic acids containing each individual error are present in the nucleic acid preparation at a lower frequency than nucleic acids having the correct sequence at the same position. Rather, error containing single strands may reanneal with a complementary strand that contains no errors or that contains one or more different errors or one or more errors at a different position. As a result, error-containing strands may end up in the form of heteroduplex molecules in the reannealed reaction product. Nucleic acid strands that are error-free may reanneal with error-containing strands or with other error-free strands. Reannealed error-free strands form homoduplexes in the reannealed sample. Accordingly, by removing heteroduplex molecules from the reannealed preparation of oligonucleotides, the amount or frequency of error-containing nucleic acids may be reduced. Any suitable method for removing heteroduplex molecules may be used, including chromatography, electrophoresis, selective binding of heteroduplex molecules, etc. In some embodiments, mismatch binding proteins that selectively (e.g., specifically) bind to heteroduplex nucleic acid molecules may be used. In some embodiments, the mismatch binding protein may be used on double-stranded oligonucleotides or polynucleotides in solution or immobilized onto a support.

By way of example, in a chain extension reaction (e.g., PCR) using primer (e.g., a universal amplification primer), the chemically synthesized oligonucleotides can serve as template strands for producing complementary strands. The resulting products can include error-free complementary strand (complementary to error-free template strand 11) and error-prone amplified complementary strand (complementary to error-prone template strand 12). Under melting conditions (e.g., an increased temperature at solid support or chip surface), the complementary strands are separated from the template strands. After shuffling, heteroduplex can be formed between an error-prone template strand and an error-free complementary strand. Heteroduplex can then be recognized and cleaved by a component (e.g., Surveyor™ endonuclease). Subsequent removal of cleaved, error-prone duplexes can result in an error-free chip surface.

In some embodiments, the oligonucleotides containing errors are removed using a MutS filtration process, for example, using MutS, a MutS homolog, or a combination thereof. It should be appreciated that error removal can make use of solid-phase MutS. In *E. coli*, the MutS protein, which appears to function as a homodimer, serves as a mismatch recognition factor. In eukaryotes, at least three MutS Homolog (MSH) proteins have been identified; namely, MSH2, MSH3, and MSH6, and they form heterodimers. For example in the yeast, *Saccharomyces cerevisiae*, the MSH2-MSH6 complex (also known as MutS alpha) recognizes base mismatches and single nucleotide insertion/deletion loops, while the MSH2-MSH3 complex (also known as MutSbeta) recognizes insertions/deletions of up to 12-16 nucleotides, although they exert substantially redundant functions. A mismatch binding protein may be obtained from recombinant or natural sources. A mismatch binding protein may be heat-stable. In some embodiments, a thermostable mismatch binding protein from a thermophilic organism may be used. Examples of thermostable DNA mismatch binding proteins include, but are not limited to: Tth MutS (from *Thermus thermophilus*), Taq MutS (from *Thermus aquaticus*), Apy MutS (from *Aquifex pyrophilus*), Tma MutS (from *Thermotoga maritima*), homologs thereof any other suitable MutS or any combination of two or more thereof.

It has been shown that MutS obtained from different species can have different affinity for a specific mismatch or for different mismatch. In some embodiments, a combination of different MutS having different affinities for different mismatch can be used.

In some embodiments, an enzyme complex using one or more repair proteins can be used. Example of repair proteins include, but are not limited to, MutS, for mismatch recognition, MutH, for introduction of a nick in the target strand, and MutL, for mediating the interactions between MutH and MutS, homologs thereof or any combinations thereof. In some embodiments, the mismatch binding protein complex is a MutHLS enzyme complex.

In some embodiments, a sliding clamp technique may be used for enriching error-free double stranded oligonucleotides. In some embodiments, MutS or homolog thereof can interact with a DNA clamp protein. Example of DNA clamp proteins include, but are not limited to, the bacterial sliding clamp protein DnaN, encoded by dnaN gene, which can function as a homodimer. In some embodiments, interaction of MutS protein, or homolog thereof, with a clamp protein can increase the effectiveness of MutS in binding mismatches.

In some embodiments, the oligonucleotides containing errors are removed using an enzyme from the S1 family of proteins, for example CELI, CELII or a homolog thereof, such as RESI, or a combination thereof. Enzymes from the S1 family of proteins can recognize base mismatches, insertion and deletion loops. In some embodiments, such enzymes can bind preferentially to Holliday junctions after which the recognition site is cleaved, either through only one or both DNA strands. In some embodiments, a thermostable equivalent of a S1 protein may be used.

In some embodiments, the oligonucleotides containing errors are removed using a small molecule, chemical or inorganic material that binds to mismatched base sites. At the mismatched site, nucleotide bases are extra-helical and can be susceptible to chemical modification reactions. Materials such permanganate, hydroxylamine, lysine, and or pentaamine ruthenium can be employed in the chemical cleavage method to modify the mismatched thymine and cytosine respectively. The resulting modified DNA can then treated with piperidine to cause a cleavage at the abasic sites. In some embodiments, specificity of cleavage can be monitored using divalent salt.

Restriction Enzymes

In some embodiments, overhangs may be generated using a type IIS restriction enzyme. Type IIS restriction enzymes are enzymes that bind to a double stranded nucleic acid at one site, referred to as the recognition site, and make a single double stranded cut outside of the recognition site. The double-stranded cut, referred to as the cleavage site, is generally situated 0-20 bases away from the recognition site. The recognition site is generally about 4-7 bp long. All type IIS restriction enzymes exhibit at least partial asymmetric recognition. Asymmetric recognition means that 5'-3' recognition sequences are different for each strand of the nucleic acid. The enzyme activity also shows polarity meaning that the cleavage sites are located on only one side of the recognition site. Thus, there is generally only one double stranded cut corresponding to each recognition site. Cleavage generally produces 1-5 nucleotide single-stranded overhangs, with 5' or 3' termini, although some enzymes produce blunt ends. Either cut is useful in the context of the invention, although in some instances those producing single-stranded overhangs are produced. To date, about 80 type IIS enzymes have been identified. Examples include but are not limited to BstF5 I, BtsC I, BsrD I, Bts I, Alw I, Bcc I, BsmA I, Ear I, Mly I (blunt), Ple I, Bmr I, Bsa I, BsmB I, Fau I, Mnl I, Sap I, Bbs I, BciV I, Hph I, Mbo II, BfuA I, BspCN I, BspM I, SfaN I, Hga I, BseR I, Bbv I, Eci I, Fok I, BceA I, BsmF I, BtgZ I, BpuE I, Bsg I, Mme I, BseG I, Bse3D I, BseM I, AcIW I, Alw26 I, Bst6 I, BstMA I, Eam1104 I, Ksp632 I, Pps I, Sch I (blunt), Bfi I, Bso31 I, BspTN I, Eco31 I, Esp3 I, Smu I, Bfu I, Bpi I, BpuA I, BstV2 I, AsuHP I, Acc36 I, Lwe I, Aar I, BseM II, TspDT I, TspGW I, BseX I, BstV1 I, Eco57 I, Eco57M I, Gsu I, and Bcg I. Such enzymes and information regarding their recognition and cleavage sites are available from commercial suppliers such as New England Biolabs, Inc. (Ipswich, Mass., U.S.A.).

In some embodiments, commercial or engineered restriction enzyme may be used. In some embodiments, type IIS restriction enzymes can be designed and engineered to produce longer overhang lengths. Designing and engineering restriction enzymes to produce longer single-stranded overhangs can allow for the joining of a larger number of oligonucleotides together to form longer nucleic acid constructs. For example, BsaI, which produces a 4 nucleotide single-stranded overhang, can be engineered to produce a 5, or 6 or longer single-stranded overhang. Increasing the length of the single-stranded overhang produced by such engineered BsaI can increase the theoretical limit of 17 nucleic acids or oligonucleotides that can be joined.

Enzymatic digestions of DNA with type II or site-specific restriction enzymes typically generate an overhang of four to six nucleotides. In some embodiments, these short cohesive ends may be sufficient for ligating two nucleic acid fragments containing complementary termini. However, when joining multiple nucleic acid fragments together, longer complementary cohesive termini may be preferred to facilitate assembly and to ensure specificity. For example, cohesive ends may be long enough to have sufficiently different sequences to prevent or reduce mispairing between similar cohesive ends. However, their length is preferably not long enough to stabilize mispairs between similar cohesive sequences. In some embodiments, a length of about 9 to about 15 bases may be used. However, any suitable length may be selected for a region that is to be used to generate a cohesive overhang. The importance of specificity may depend on the number of different fragments that are being assembled simultaneously. Also, the appropriate length required to avoid stabilizing mispaired regions may depend on the conditions used for annealing different cohesive ends.

Apparatus

Aspects of the invention relate to apparatus for high-throughput synthesis of nucleic acids. It should be appreciated that in some instances the reagent used during the synthesis can be viscous. In particular, the chemical phosphorylation reagent used the methods described herein is viscous even after dilution. The viscosity of the reagent can impact the synthesis of 3'-phosphorylated nucleic acids as at least some of the target features on the array may not receive the chemical phosphorylation reagent and may not attach the nucleotide during the synthesis. In some embodiments, the apparatus can be adapted to the liquid viscosity employed in some of the methods described herein. For example, the apparatus may be designed to include a cell or sensor recording the microenvironment to monitor if the reagent has been added or not.

In some embodiments, two on-chip interdigitated capacitors with platinum layering on top, provide differential measurement of the CMOS unit cell change. The unit cell forms an extending floating gate whereby the collocated control gate readout is multiplexed back to the control software. The control software multiplexes from five distinct locations on a CMOS chip and pauses transmission of an electrode activation command for next chemical firing until a readback is received from all five locations.

Figure 1A:
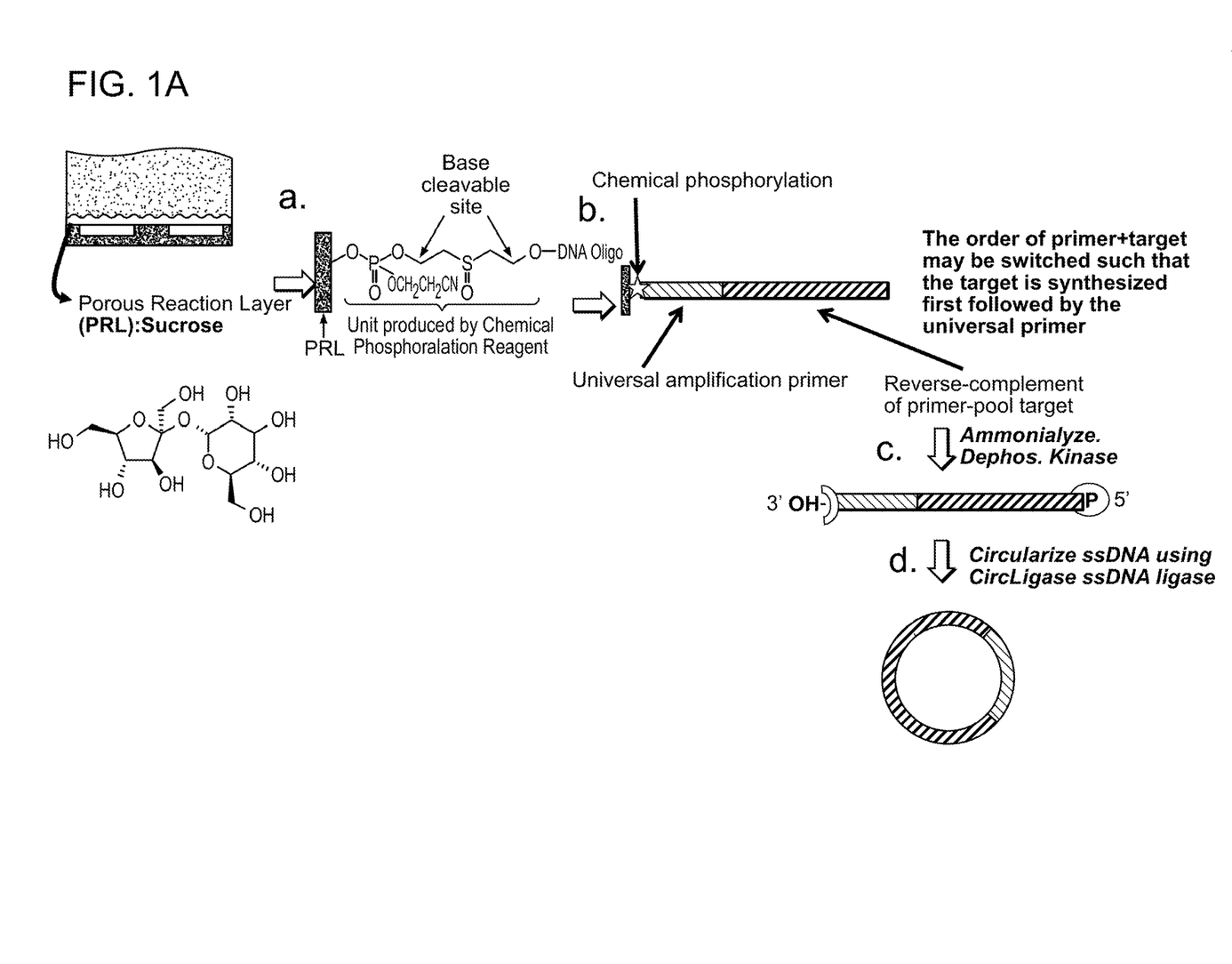
FIG. 1A illustrates an exemplary method for generating circular template for the synthesis of high fidelity oligonucleotides according to a non-limiting embodiment.

Method of Synthesizing High Fidelity Oligonucleotides Using Template Oligonucleotide Circularization and Rolling Circle Amplification In some aspects, the methods employ a circular template and rolling-circle amplification. In some embodiments and referring to FIG. 1A, the nucleic acids can be synthesized in situ on a solid support. The solid support can have a porous reaction layer (PRL) having hydroxyl reactive groups. For example, the reaction layer can comprise sucrose. According to some embodiments, the porous reaction layer can be chemically modified and be coupled to a chemical phosphorylation reagent (FIG. 1A, a.).

According to various embodiments, the plurality of nucleic acids to be synthesized is designed to have the reverse complement of the target oligonucleotide sequence of interest and a primer binding region. For example, the nucleic acids are designed to have a primer binding region at the 3' end of the reverse complement oligonucleotide or at the 5' end of the reverse complement oligonucleotide. Accordingly, the 3' end of the primer binding region or the 3' end of the reverse complement oligonucleotide can be phosphorylated during synthesis (FIG. 1A, b.). After synthesis, the plurality of nucleic acids can be released in solution. In some embodiments, the plurality of 3'-phosphorylated nucleic acids is released in a single pool. In some embodiments, the 3'-phosphorylated nucleic acids are dephosphorylated, for example, using a phosphatase that can catalyze the removal of the 3' phosphate. In some embodiments, the dephosphorylated nucleic acids can be phosphorylated using, for example, a T4 kinase capable of transferring the phosphate from ATP to the 5' hydroxyl terminus of the nucleic acid (FIG. 1A, c.). The 5'-phosphorylated nucleic acids can then be circularized (FIG. 1A, d.). Circularization can be catalyzed by a single-stranded ligase that catalyzes intramolecular ligation of the single stranded nucleic acid having a 5'-phosphate and a 3'-hydroxyl group. For example, CircLigase™ ssDNA Ligase (Epicentre) can be used to circularize the single-stranded nucleic acid.

Some aspects of the invention relate to synthesis of high fidelity oligonucleotides from a circularized nucleic acid comprising a primer binding region and a target sequence. In some embodiments, the target sequence can be the reverse complement sequence.

Amplification reactions according to some aspects of the invention utilize a hairpin primer. In some embodiments, the primer is a self-hairpinning primer. For example, the primer can comprise self-complementary termini. When under the hairpin configuration, the primer comprises a single-stranded "loop" and a double-stranded "stem". The hairpin primer can be designed to comprise dT biotin. In some embodiments, the primers comprise internal dT biotin.

In some embodiments, the primer binding region is a long amplification sequence having complementary termini. The amplification sequence can be self-hairpinning. The amplification sequence can be at least 100 bps long. For example, the amplification sequence can be about 110, 120, 130, 140, 150, 160, 170, 180, 190, 200 bps or more bps long. The amplification sequence can be a universal or semi-universal sequence. It should be appreciated that the nucleic acid sequence comprising the long amplification sequence can be synthesized in situ on the array as described herein. However, in some embodiments, the amplification sequence can be ligated to an oligonucleotide post synthesis. For example, the oligonucleotide can be synthesized on a solid support such as an array and the amplification sequence can be ligated enzymatically using a ssDNA ligase (e.g. ThermoPhage™ ssDNA ligase from Prokazyme) or chemically (e.g. via a sulfanylethylanilide peptide). In some embodiments, the oligonucleotides can be released from the solid support prior to the ligation of the amplification sequence. Release from the solid support can be effected chemically or photochemical depending of the choice of linkers.

The circular nucleic acid can be amplified by rolling circle amplification. A rolling circle amplification primer can be provided, the primer having a sequence complementary to the primer binding region of the nucleic acid. The complementary portion of the primer can have any desired sequence. In some embodiments, the primer is designed to comprise a sequence complementary to the primer binding sequence, and self-complementary termini having a restriction enzyme recognition site, can be annealed to the circularized nucleic acid under conditions promoting annealing of the primer to the primer binding sites and avoiding self-hairpinning (i.e. intramolecular association of the complementary termini).

Figure 1B:
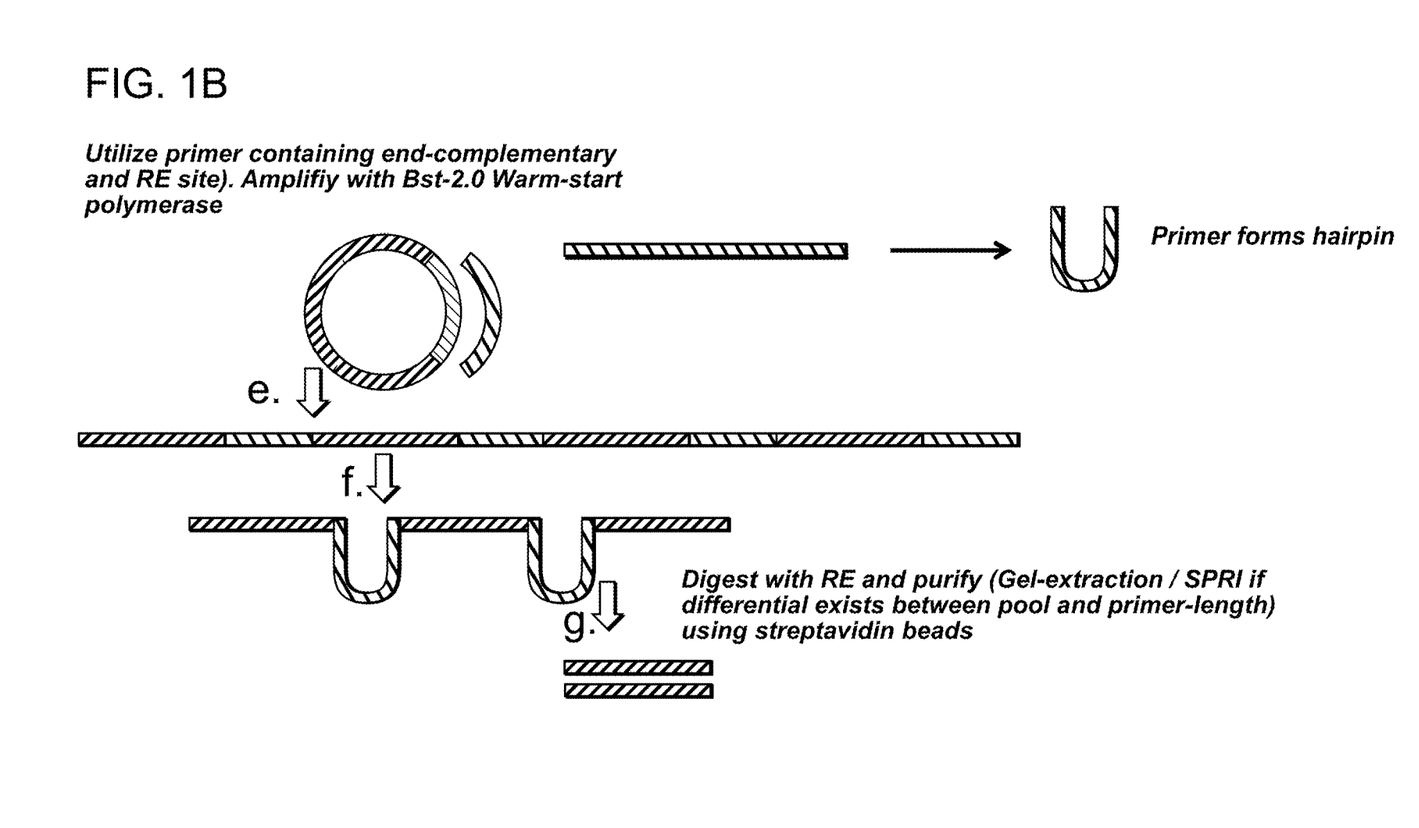
FIG. 1B illustrates the synthesis of high fidelity oligonucleotides by rolling circle amplification according to a non-limiting embodiment.

After annealing of the primer to the primer binding region of the nucleic acid, the nucleic acid is amplified under conditions suitable for amplification. In an exemplary embodiment, Bst 2.0 WarmStart DNA Polymerase can be used. The circular nucleic acid, when amplified, can generate long DNA molecules containing multiple repeats of sequences complementary to the amplification circular nucleic acid, also referred herein as tandem sequences (FIG. 1B, e.). The tandem sequences contain sequences complementary to the primer binding region(s) or primer binding sequence(s). The tandem sequences can be incubated under conditions suitable for intramolecular association of the self-complementary termini or self-hairpinning (FIG. 1B, f.). Self-hairpinning of the primers along the tandem sequences allows for the formation of partially double-stranded sequences designed to have a restriction enzyme recognition site. The resulting product can be digested with the suitable restriction enzyme to remove the primers binding sequences and release the oligonucleotide sequences of interest. (FIG. 1B, g.).

Figure 2:
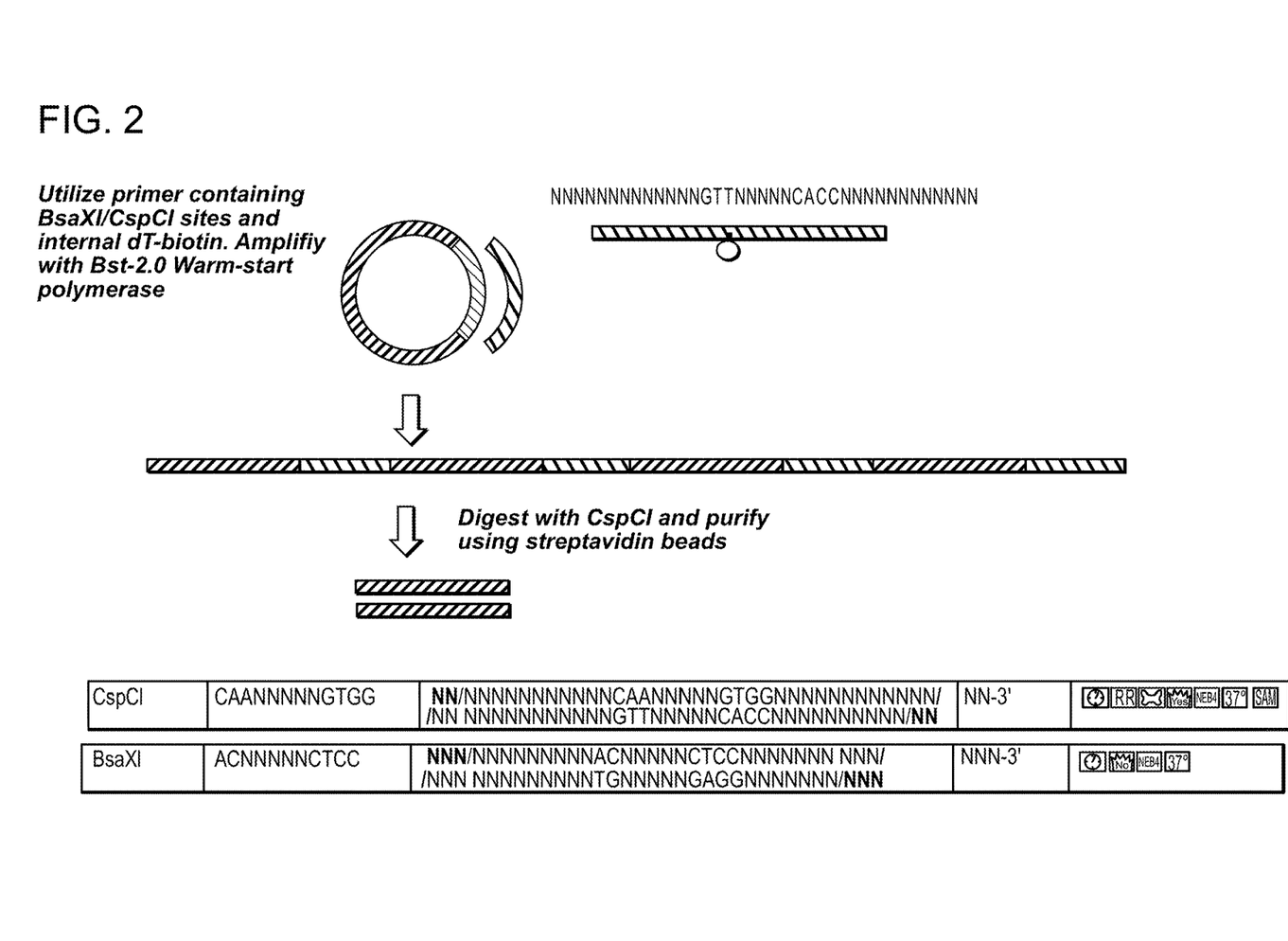
FIG. 2 illustrates an exemplary method for the synthesis of high fidelity oligonucleotides using a circular template and rolling circle amplification according to a non-limiting embodiment.

In some embodiments, the oligonucleotides can be purified. For example, the oligonucleotides can be purified by gel extraction or using beads, such as magnetic, paramagnetic or streptavidin beads. In some embodiments, the primer comprises dT biotin (See FIG. 2). After amplification using such biotinylated primers, the amplification products can be affinity purified by removing the primers using streptavidin (e.g., bound to a bead, column, or other surface). For example, Solid Phase Reversible Immobilization (SPRI) beads from Beckman Coulter can be used. In some embodiments, depending on the length of the nucleic acids, a double-sided SPRI purification can be used (e.g. for example when long amplification sequences are used). Using standard magnetic capture, the solution is then removed followed by subsequent washing of the conjugated beads. In some embodiments, the beads can be configured for either hybridization or ligation based capture using double-stranded sequences on the bead.

One of skill in the art would appreciate the methods of synthesis described herein have particular advantages in relation to the rolling circle amplification and the use of a single primer. In particular, the method of amplifying uses rolling circle amplification under conditions suitable for equimolar amplification of the nucleic acids. Rolling circle amplification is then carried out with a DNA polymerase. Any DNA polymerase capable of providing a superior rate of DNA synthesis and high processivity which allows rapid replication through regions of high GC content, hairpin structures and other regions of secondary structure, and regions that normally slow replication due to local sequence context effects can be used. In some embodiments, a strand displacing polymerase can be used. In an exemplary embodiment, Bst 2.0 WarmStart DNA Polymerase can be used and provides the advantage that temperature conditions do not need to be changed for the amplification reaction. An additional advantage of the methods described herein is that because of the use of a single primer, the nucleic acid is shorter thereby reducing the extent of the increased amplification errors that tend to occur in long amplification product.

In some embodiments, primers containing internal dT biotin can be used. In some embodiments, primers containing for example BsaXI/CspCI sites can be used (See FIG. 2). After amplification, the amplified product can be digested with CspCI. In some embodiments, the oligonucleotides can be purified. For example, the oligonucleotides can be purified by gel extraction or using beads, such as magnetic, paramagnetic or streptavidin beads.

Method of Synthesizing High Fidelity Oligonucleotides Using Cleavage of Abasic Sites According to some embodiments, the plurality of nucleic acids to be synthesized is designed to have a central oligonucleotide sequence of interest and a 5' amplification flanking region and a 3' amplification region. In some embodiments, the plurality of single-stranded nucleic acids comprises nucleic acids molecules having the positive strand and nucleic acids molecules having the negative strand. The flanking sequences are designed for amplification and are not intended to be part of the final oligonucleotide sequence or incorporated into the assembled nucleic acid. The flanking amplification sequences may be used as primer binding sequences to amplify a plurality of different assembly oligonucleotides that share the same amplification sequences but have different central assembly sequences. As used herein, the terms "central oligonucleotide sequence", "oligonucleotide of interest", "construction oligonucleotide" and "payload" are used interchangeably. In various embodiments, the central oligonucleotide sequence can be padded at the 5' end or the 3' end with a padding sequence of (m)

nucleotides M ($M_m$). In some embodiments, the padding sequence can be 4 bases long, 5 bases long, 6 bases long, 7 bases long, 8 bases long, 9 bases long, and 10 bases long or longer. For example, each payload can be padded so as to add a padding sequence at the 3' end of the payload sequence.

Figure 3:
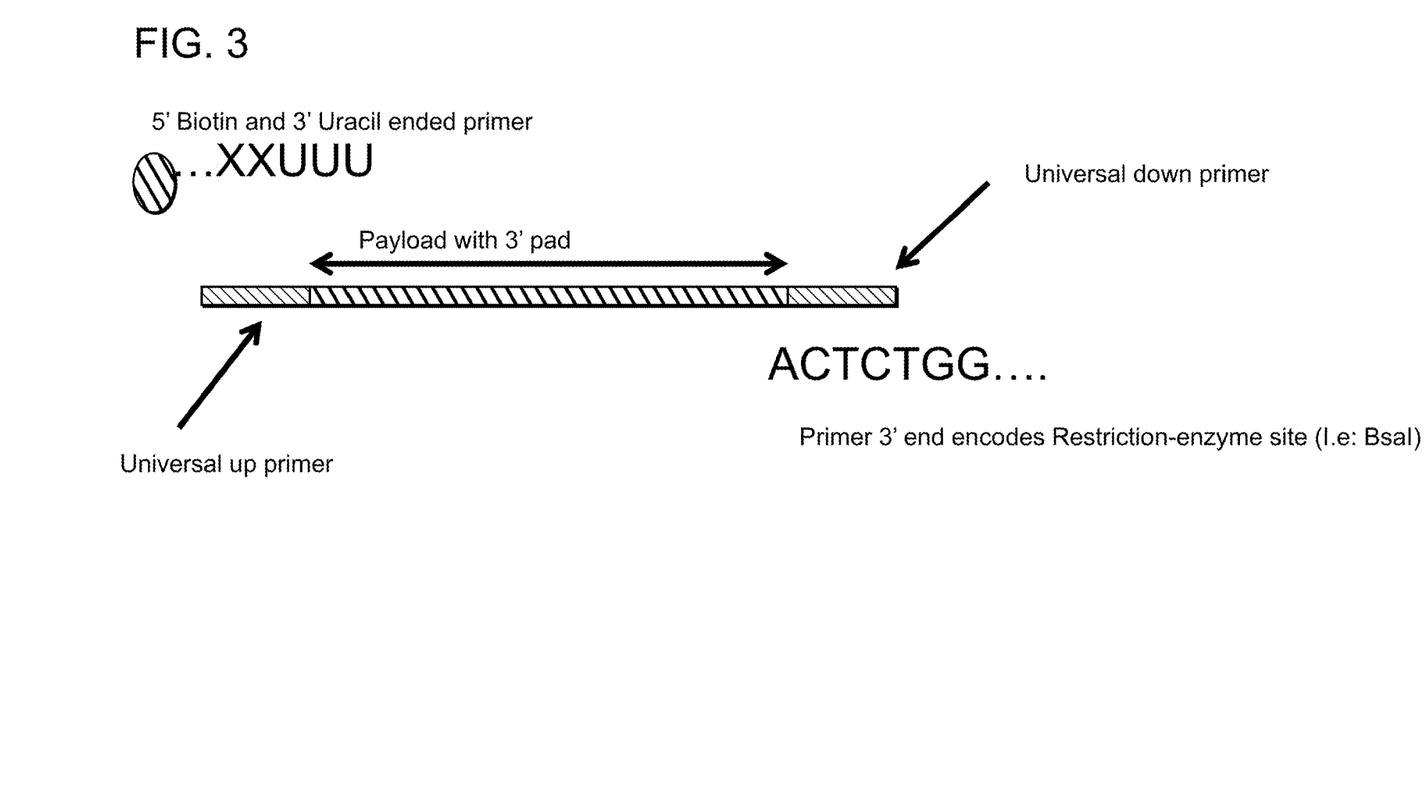
FIG. 3 illustrates an exemplary method for the synthesis of high fidelity oligonucleotides according to a non-limiting embodiment.

In some embodiments, the universal or semi-universal forward and reverse primers can be used to amplify the nucleic acid sequences. In various embodiments, the forward primer can be designed to introduce an abasic site as described herein and the reverse primer can be designed to have a restriction enzyme site. In some embodiments, at least one primer is designed to have an affinity tag. For example, the forward primer can be designed to have 5' biotin and at least one uracil at its 3' end and the reverse primer is designed to have a restriction recognition site for a type IIs restriction enzyme (e.g. BsaI) at its 3' end (FIG. 3). Alternatively, the forward primer can be designed to have a restriction enzyme site at its 5' end and the reverse primer is designed to have at least one uracil at its 5' end and a tag, such as biotin, at its 3' end.

According to various embodiments, the double-stranded nucleic acids can be generated by amplification and shuffling or by annealing the reverse complements strands.

In some embodiments, the methods further comprise removing base mismatched nucleic acids from a population of error-free nucleic acids. The methods generally comprise the steps of contacting double-stranded nucleic acids with a mismatch recognition protein, and isolating the double-stranded nucleic acids that did not bind the mismatch recognition protein. The isolating step can comprises removal of the error-free duplexes from the population of error-containing nucleic acids, or the removal the error-containing nucleic acids that interact with the mismatch binding protein. In some embodiments, the mismatch recognition protein can be immobilized on a solid support, which results directly in the separation of error-free nucleic acids from the error-containing nucleic acids.

In various embodiments, the methods comprise removing the flanking amplification sequence comprising the restriction enzyme recognition site by enzymatic cleavage. Digestion with the restriction enzyme can be included before or after the error reduction step. In some embodiments, the digested fragment having the affinity tag can be captured on a support. For example, the biotinylated fragment can be captured on streptavidin beads. The double stranded nucleic acids can then be denatured to remove the secondary strand. After denaturation, the single-stranded nucleic acid can be released from the support by cleavage of the abasic sites.

Assembly

Aspects of the invention may be used to enhance different types of nucleic acid assembly reactions (e.g., multiplex nucleic acid assembly reactions). Aspects of the invention may be used in combination with one or more assembly reactions described in, for example, Carr et al., 2004, Nucleic Acids Research, Vol. 32, No 20, e162 (9 pages); Richmond et al., 2004, Nucleic Acids Research, Vol. 32, No 17, pp. 5011-5018; Caruthers et al., 1972, J. Mol. Biol. 72, 475-492; Hecker et al., 1998, Biotechniques 24:256-260; Kodumal et al., 2004, PNAS Vol. 101, No. 44, pp. 15573-15578; Tian et al., 2004, Nature, Vol. 432, pp. 1050-1054; and U.S. Pat. Nos. 6,008,031 and 5,922,539, the disclosures of which are incorporated herein by reference. Aspects of the invention may be used in combination with one or more assembly reactions described in, for example, U.S. Ser. No. 13/592,827 (U.S. Publication number US 2013-0059296), and International Application No. PCT/US11/060243, which are incorporated by reference in their entirety. It should be appreciated that synthesis and assembly methods (including, for example, oligonucleotide synthesis, stepwise assembly, multiplex nucleic acid assembly, hierarchical assembly of nucleic acid fragments, or any combination thereof) may be performed in any suitable format, including in a reaction tube, in a multi-well plate, on a surface, on a column, in a microfluidic device (e.g., a microfluidic tube), a capillary tube, etc. For example, some embodiments, the target nucleic acid can be assembled by "recursive assembly" or "hierarchical assembly." In this embodiment, the target nucleic acid is divided first into two or more overlapping nucleic acid fragments (or subassembly fragments). Each nucleic acid fragment is then subdivided into two or more overlapping smaller nucleic acid fragments.

In some embodiments, the nucleic acids synthesized according to the methods of the invention can be assembled using origami assembly or isothermal origami assembly described in, for example, Marchi et al. (ACS Nano, 2013, Vol. 7, pp 903-910), Jungmann et al. (J. Am. Chem. Soc., 2008, Vo. 130, pp 10062-10063) and Hogberg et al (J. Am. Chem. Soc., 2009, Vol. 131, 9154-9155).

Automated Applications

Aspects of the methods and devices provided herein may include automating one or more acts described herein. In some embodiments, one or more steps of an amplification and/or assembly reaction may be automated using one or more automated sample handling devices (e.g., one or more automated liquid or fluid handling devices). Automated devices and procedures may be used to deliver reaction reagents, including one or more of the following: starting nucleic acids, buffers, enzymes (e.g., one or more ligases and/or polymerases), nucleotides, salts, and any other suitable agents such as stabilizing agents. Automated devices and procedures also may be used to control the reaction conditions. For example, an automated thermal cycler may be used to control reaction temperatures and any temperature cycles that may be used. In some embodiments, a scanning laser may be automated to provide one or more reaction temperatures or temperature cycles suitable for incubating polynucleotides. Similarly, subsequent analysis of assembled polynucleotide products may be automated. For example, sequencing may be automated using a sequencing device and automated sequencing protocols. Additional steps (e.g., amplification, cloning, etc.) also may be automated using one or more appropriate devices and related protocols. It should be appreciated that one or more of the device or device components described herein may be combined in a system (e.g., a robotic system) or in a micro-environment (e.g., a micro-fluidic reaction chamber). Assembly reaction mixtures (e.g., liquid reaction samples) may be transferred from one component of the system to another using automated devices and procedures (e.g., robotic manipulation and/or transfer of samples and/or sample containers, including automated pipetting devices, micro-systems, etc.). The system and any components thereof may be controlled by a control system.

Accordingly, method steps and/or aspects of the devices provided herein may be automated using, for example, a computer system (e.g., a computer controlled system). A computer system on which aspects of the technology provided herein can be implemented may include a computer for any type of processing (e.g., sequence analysis and/or automated device control as described herein). However, it should be appreciated that certain processing steps may be provided by one or more of the automated devices that are part of the assembly system. In some embodiments, a computer system may include two or more computers. For example, one computer may be coupled, via a network, to a second computer. One computer may perform sequence analysis. The second computer may control one or more of the automated synthesis and assembly devices in the system. In other aspects, additional computers may be included in the network to control one or more of the analysis or processing acts. Each computer may include a memory and processor. The computers can take any form, as the aspects of the technology provided herein are not limited to being implemented on any particular computer platform. Similarly, the network can take any form, including a private network or a public network (e.g., the Internet). Display devices can be associated with one or more of the devices and computers. Alternatively, or in addition, a display device may be located at a remote site and connected for displaying the output of an analysis in accordance with the technology provided herein. Connections between the different components of the system may be via wire, optical fiber, wireless transmission, satellite transmission, any other suitable transmission, or any combination of two or more of the above.

Each of the different aspects, embodiments, or acts of the technology provided herein can be independently automated and implemented in any of numerous ways. For example, each aspect, embodiment, or act can be independently implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of the embodiments of the technology provided herein comprises at least one computer-readable medium (e.g., a computer memory, a floppy disk, a compact disk, a tape, etc.) encoded with a computer program (i.e., a plurality of instructions), which, when executed on a processor, performs one or more of the above-discussed functions of the technology provided herein. The computer-readable medium can be transportable such that the program stored thereon can be loaded onto any computer system resource to implement one or more functions of the technology provided herein. In addition, it should be appreciated that the reference to a computer program which, when executed, performs the above-discussed functions, is not limited to an application program running on a host computer. Rather, the term computer program is used herein in a generic sense to reference any type of computer code (e.g., software or microcode) that can be employed to program a processor to implement the above-discussed aspects of the technology provided herein.

It should be appreciated that in accordance with several embodiments of the technology provided herein wherein processes are stored in a computer readable medium, the computer implemented processes may, during the course of their execution, receive input manually (e.g., from a user).

Accordingly, overall system-level control of the assembly devices or components described herein may be performed by a system controller which may provide control signals to the associated nucleic acid synthesizers, liquid handling devices, thermal cyclers, sequencing devices, associated robotic components, as well as other suitable systems for performing the desired input/output or other control functions. Thus, the system controller along with any device controllers together form a controller that controls the operation of a nucleic acid assembly system. The controller may include a general purpose data processing system, which can be a general purpose computer, or network of general purpose computers, and other associated devices, including communications devices, modems, and/or other circuitry or components to perform the desired input/output or other functions. The controller can also be implemented, at least in part, as a single special purpose integrated circuit (e.g., ASIC) or an array of ASICs, each having a main or central processor section for overall, system-level control, and separate sections dedicated to performing various different specific computations, functions and other processes under the control of the central processor section. The controller can also be implemented using a plurality of separate dedicated programmable integrated or other electronic circuits or devices, e.g., hard wired electronic or logic circuits such as discrete element circuits or programmable logic devices. The controller can also include any other components or devices, such as user input/output devices (monitors, displays, printers, a keyboard, a user pointing device, touch screen, or other user interface, etc.), data storage devices, drive motors, linkages, valve controllers, robotic devices, vacuum and other pumps, pressure sensors, detectors, power supplies, pulse sources, communication devices or other electronic circuitry or components, and so on. The controller also may control operation of other portions of a system, such as automated client order processing, quality control, packaging, shipping, billing, etc., to perform other suitable functions known in the art but not described in detail herein.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

EXAMPLES

Example 1

Figure 4:
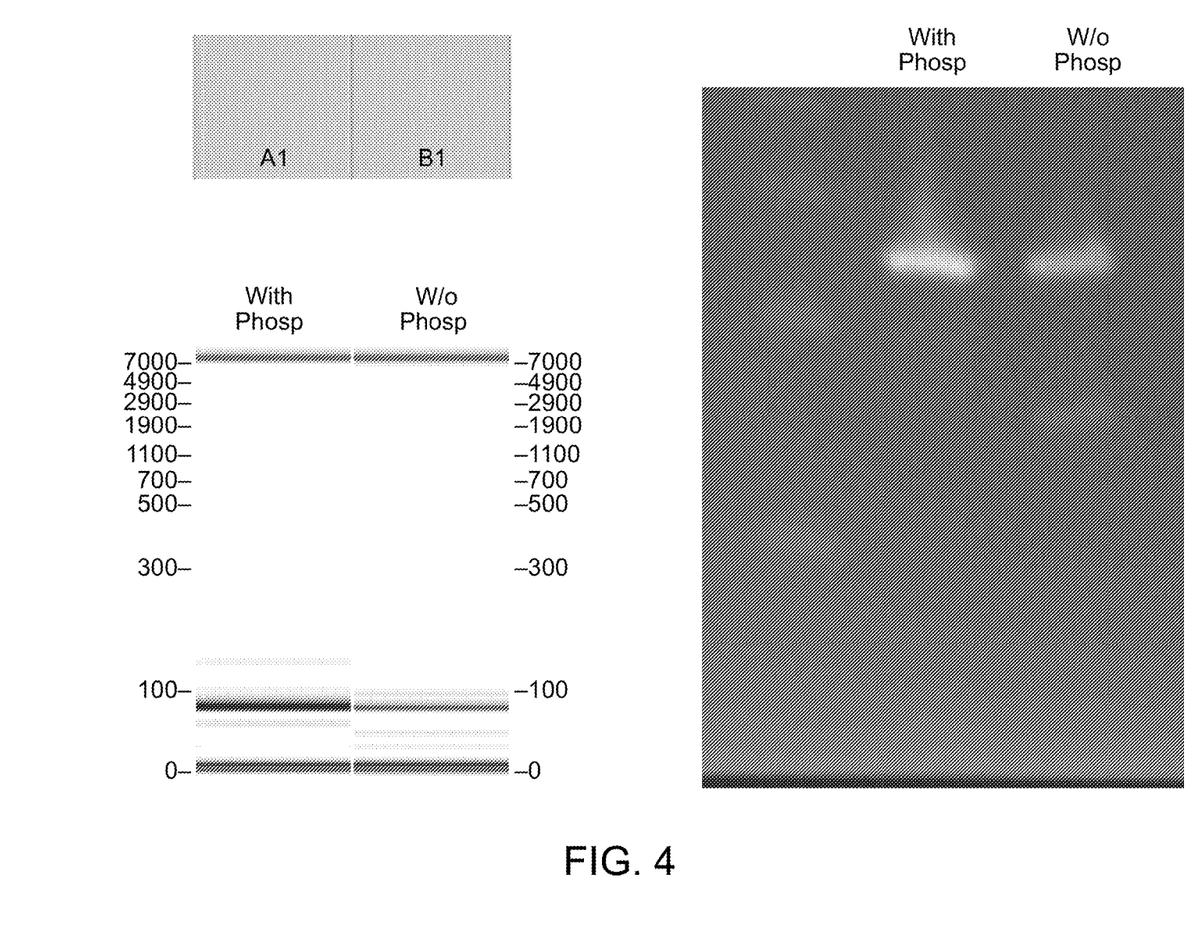
FIG. 4 illustrates a modified 3'phosphate synthesis according to one embodiment of the invention.

A 69-mer oligonucleotide was synthesized on an array with or without 3' phosphate. The chemical phosphorylation reagent was supplied in lieu of a standard amidite at 0.1M in acetonitrile during synthesis. The reagent was added as the first base of synthesis in a 3'-5' synthesis setup. Synthesis was performed with final DMT-on. This DMT group was then later removed via processing with 80% acetic acid. The oligonucleotide was cleaved from the array according to the methods described herein and amplified by PCR. Subsequent usage of this material as template in a PCR reaction yielded the expected product (FIG. 4).

Example 2

Figure 5:
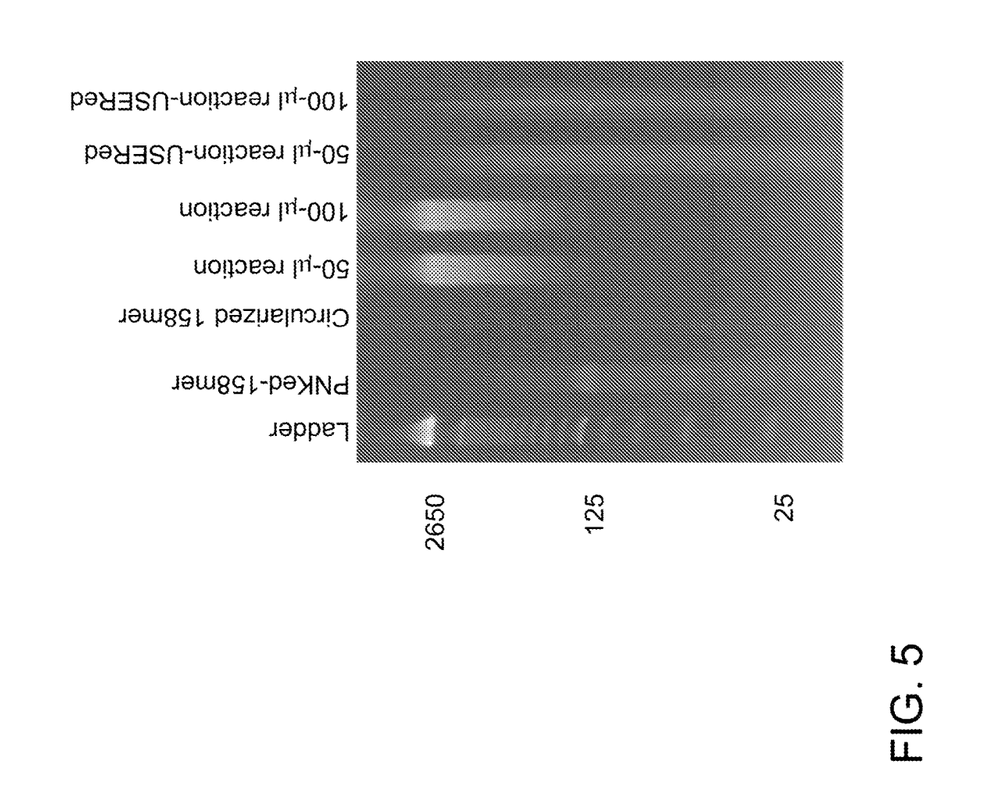
FIG. 5 illustrates dU-Rolling Circle Amplification according to one embodiment of the invention.

A 158-mer ultramer was provided (IDT). The oligonucleotide was phosphorylated enzymatically at its 5' end using a polynucleotide kinase. The oligonucleotide was circularized using Circligase (Epicentre). The circular oligonucleotide was amplified using a primer and using a strand displacing polymerase (Bst 2.0 Warmstart polymerase (New England BioLabs)) in the presence of dNTP and dU for 4 hours. The resulting dU containing amplification products were cleaved using USER™ enzyme system (New England BioLabs) for 2 hours. FIG. 5 shows the results at using samples taken at different steps of the synthesis.

Example 3

Figure 6:
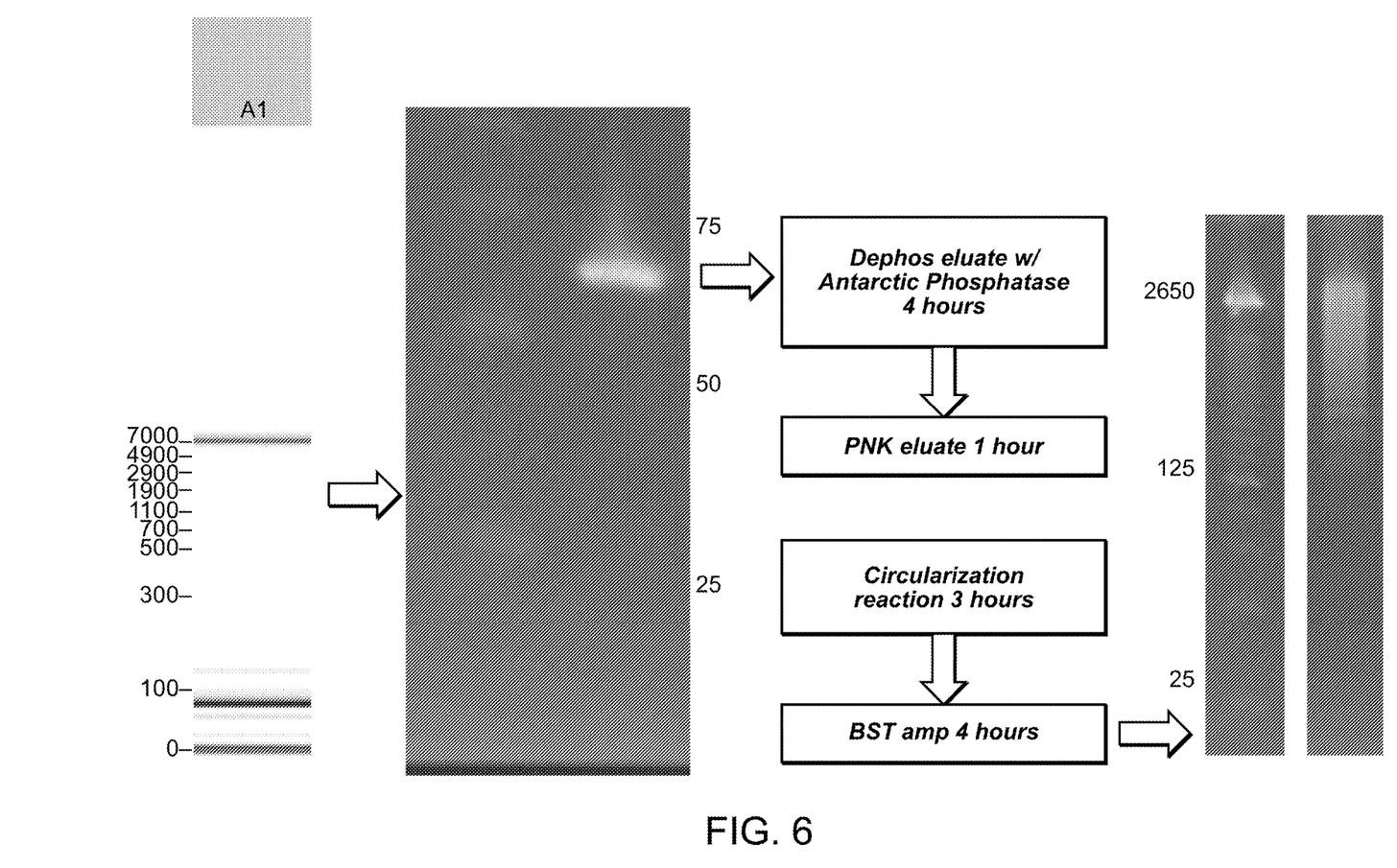
FIG. 6 illustrates 3' phosphate synthesis and Rolling Circle Amplification according to one embodiment of the invention.

A 69-mer oligonucleotide was synthesized on an array with or without 3' phosphate as described in Example 1. The oligonucleotide was cleaved from the array, dephosphorylated to remove the 3' phosphate using Antarctic phosphatase (New England BioLabs) and phosphorylated to add a 5' phosphate (1 hour), circularized (3 hours) according to the methods described herein. The circular oligonucleotide was amplified by rolling circle amplification as described in Example 2 (Bst 2.0 Warmstart polymerase for 4 hours). FIG. 6 shows results before the phosphatase step and after the amplification step.

EQUIVALENTS

The present invention provides among other things novel methods and devices for high-fidelity gene assembly. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

INCORPORATION BY REFERENCE

All publications, patents and sequence database entries mentioned herein are hereby incorporated by reference in their entirety as if each individual publication or patent was specifically and individually indicated to be incorporated by reference. Reference is made to U.S. Provisional Application No. 61/778,973, filed Mar. 13, 2013, entitled "Compositions, Methods And Apparatus For Oligonucleotides Synthesis" which is incorporated by reference in its entirety.

What is claimed is:
1. A method for synthesizing high fidelity target oligonucleotides, the method comprising:

a. providing an array comprising a plurality of nucleic acids, each nucleic acid having a sequence comprising a template oligonucleotide sequence and a primer binding sequence, wherein the template oligonucleotide sequence is a reverse complement of the target oligonucleotide;
b. releasing the plurality of nucleic acids from the array;
c. circularizing the plurality of nucleic acids;
d. providing a primer, wherein the primer comprises a sequence complementary to the primer binding sequence, a restriction enzyme recognition site and self-complementary termini, under conditions promoting annealing of the primer to the primer binding sites;
e. amplifying the circularized nucleic acids in a rolling-circle amplification reaction using the primer, thereby forming single-stranded tandem nucleic acid sequences;
f. promoting hairpin formation of the primer wherein the restriction enzyme recognition site is formed within a double-stranded portion of the hairpin;
g. removing the primer binding sequences of the single-stranded tandem nucleic acid sequences by enzymatic cleavage using a suitable restriction enzyme; and
h. isolating the target oligonucleotides.

2. The method of claim 1 wherein in the step of releasing the plurality of nucleic acids is released in a pool.

3. The method according to claim 1 wherein the plurality of nucleic acids is immobilized on the array by their 3' terminus.

4. The method according to claim 1 wherein the plurality of nucleic acids is synthesized on the array in a 3'-5' direction.

5. The method according to claim 1 wherein the plurality of nucleic acids is synthesized on the array in a 5'-3' direction.

6. The method according to claim 1 wherein the primer binding sequence is at least 100 bps long.

7. The method according to claim 1 wherein in the step of providing the array, the array comprises a plurality of template oligonucleotides and the primer binding sequence is ligated to each of the plurality of the template oligonucleotides.

8. The method according to claim 1 wherein, in the step of providing the array, the array comprises a porous reaction layer coupled to a phosphorylation reagent.

9. The method according to claim 1 wherein the primer binding site is 3' or 5' of the template oligonucleotide sequence.

10. The method according to claim 1 wherein the plurality of nucleic acids is phosphorylated at the 3' end and wherein the step of releasing further comprises dephosphorylating the 3' end of the nucleic acids and phosphorylating the 5' end of the nucleic acids.

11. The method according to claim 1 wherein the step of circularizing is in the presence of a ligase.

12. The method according to claim 1 further comprising purifying the target oligonucleotides.

13. The method according to claim 1 wherein the primers contain dT-biotin and wherein, in the step of isolating, the oligonucleotides are purified using streptavidin beads.

14. The method of claim 1 wherein in step (a) the plurality of nucleic acids is synthesized on an array.

* * * * *